United States Patent
Lund et al.

(10) Patent No.: US 12,217,873 B2
(45) Date of Patent: Feb. 4, 2025

(54) NEURAL INPUT/OUTPUT DEVICE (NIOD) SYSTEMS AND METHODS

(71) Applicants: Peter Lund, Clackamas, OR (US); Julius Jockusch, Oregon City, OR (US); Albert Chi, Oregon City, OR (US); Robert Armiger, Catonsville, MD (US); Matthew Fifer, Columbia, MD (US); Brock Wester, Catonsville, MD (US); Andrew Badger, Oregon City, OR (US)

(72) Inventors: Peter Lund, Clackamas, OR (US); Julius Jockusch, Oregon City, OR (US); Albert Chi, Oregon City, OR (US); Robert Armiger, Catonsville, MD (US); Matthew Fifer, Columbia, MD (US); Brock Wester, Catonsville, MD (US); Andrew Badger, Oregon City, OR (US)

(*) Notice: Subject to any disclaimer, the term of this patent is extended or adjusted under 35 U.S.C. 154(b) by 0 days.

(21) Appl. No.: 18/457,994

(22) Filed: Aug. 29, 2023

(65) Prior Publication Data

US 2023/0402190 A1    Dec. 14, 2023

Related U.S. Application Data

(62) Division of application No. 17/152,534, filed on Jan. 19, 2021, now abandoned.

(60) Provisional application No. 62/962,078, filed on Jan. 16, 2020.

(51) Int. Cl.
| | | |
|---|---|---|
| G16H 50/50 | (2018.01) | |
| A61N 1/05 | (2006.01) | |
| G06N 3/044 | (2023.01) | |
| G06N 3/045 | (2023.01) | |
| G06N 3/08 | (2023.01) | |
| G16H 40/20 | (2018.01) | |
| G16H 40/67 | (2018.01) | |

(52) U.S. Cl.
CPC ............ *G16H 50/50* (2018.01); *G06N 3/044* (2023.01); *G06N 3/045* (2023.01); *G06N 3/08* (2013.01); *G16H 40/20* (2018.01); *G16H 40/67* (2018.01); *A61N 1/0556* (2013.01)

(58) Field of Classification Search
CPC ........ G16H 50/50; G16H 40/67; G16H 40/20; G06N 3/08; G06N 3/045; G06N 3/044; A61N 1/0556

See application file for complete search history.

(56) References Cited

U.S. PATENT DOCUMENTS

| | | | |
|---|---|---|---|
| 2017/0024540 A1 | 1/2017 | Han et al. | |
| 2020/0121544 A1* | 4/2020 | George | A61H 21/00 |
| 2020/0360655 A1* | 11/2020 | Shuster | A61F 2/72 |

OTHER PUBLICATIONS

\M. Thøgersen et al., Removing own-limb visual input using mixed reality (MR) produces a "telescoping" illusion in healthy individuals, 347 Behavioural Brain Research 263-271 (Year: 2018).*

(Continued)

*Primary Examiner* — Jordan L Jackson
(74) *Attorney, Agent, or Firm* — McCoy Russell LLP

(57) ABSTRACT

A system can include: a neural input/output device (NIOD) implanted in a user; a real-time engine communicatively coupled with the NIOD; and a three-dimensional (3D) object communicatively coupled with the NIOD.

1 Claim, 18 Drawing Sheets

(56) References Cited

OTHER PUBLICATIONS

Schmalzl et al., "Pulling telescoped phantoms out of the stump": Manipulating the perceived position of phantom limbs using a full-body illusion, 5 Front. Hum. Neurosci. 1-12 (Nov. 2011) (Year: 2011).*
Saito et al., The Method of Reducing Phantom Limb Pain Using Optical See-Through Head Mounted Display, 2019 IEEE Conference on Virtual Reality and 3D User Interfaces 1560-1562 (Year: 2019).*
Mott, J. et al., "The efficacy of an augmented virtual reality system to alleviate pain in children undergoing burns dressing changes: a randomised controlled trial," Burns, vol. 34, No. 6, Sep. 2008, Available Online Mar. 5, 2008, 6 pages.
Aparecida De Assis, G et al., "An augmented reality system for upper-limb post-stroke motor rehabilitation: a feasibility study," Disability and Rehabilitation. Assistive Technology, vol. 11, No. 6, Aug. 2016, Available Online Nov. 4, 2014, 8 pages.
Ortiz-Catalan, M. et al., "Phantom motor execution facilitated by machine learning and augmented reality as treatment for phantom limb pain: a single group, clinical trial in patients with chronic intractable phantom limb pain," Lancet, Dec. 10, 2016, Available Online Dec. 2, 2016, 10 pages.

* cited by examiner

300

600

900

1000

1300

NEURAL INPUT/OUTPUT DEVICE (NIOD) SYSTEMS AND METHODS

CROSS REFERENCE TO RELATED APPLICATION

The present application is a divisional of U.S. Non-Provisional patent application Ser. No. 17/152,534, entitled "VIRTUAL REALITY-BASED SYSTEMS AND METHODS", filed on Jan. 19, 2021. U.S. Non-Provisional patent application Ser. No. 17/152,534 claims priority to and the benefit of U.S. Provisional Application No. 62/962,078, filed on Jan. 16, 2020 and titled VIRTUAL REALITY-BASED SYSTEMS AND METHODS. The entire contents of the above-listed applications are hereby incorporated by reference for all purposes.

BACKGROUND

Virtual reality (VR) has become commonplace in a wide variety of industries and applications in recent years. There remains a need for improved virtual reality-based systems and methods for use by and for patients in various types of medical diagnoses and treatment plans.

DETAILED DESCRIPTION

The disclosed technology is generally directed to various types of targeted virtual reality (VR) diagnostic tools and techniques and corresponding therapies.

Targeted VR Symptom Therapy

In certain embodiments, VR Targeted Symptom Therapy generally involves the applying of visualizations to an identified area of pain or other symptoms. Identified below are three use cases but it will be appreciated that one having ordinary skill in the art will readily recognize that this type of therapy could be applied to virtually any type of symptom in any location of the patient's body.

The user may be represented in VR by their avatar and this avatar may be mapped to the user's physical body, e.g., "treated" in a third person view. The area of pain, injury, or disease may be represented within the avatar. Visualized therapies may then be applied to the target area, and the target area will typically respond to the therapies.

Figure 1:
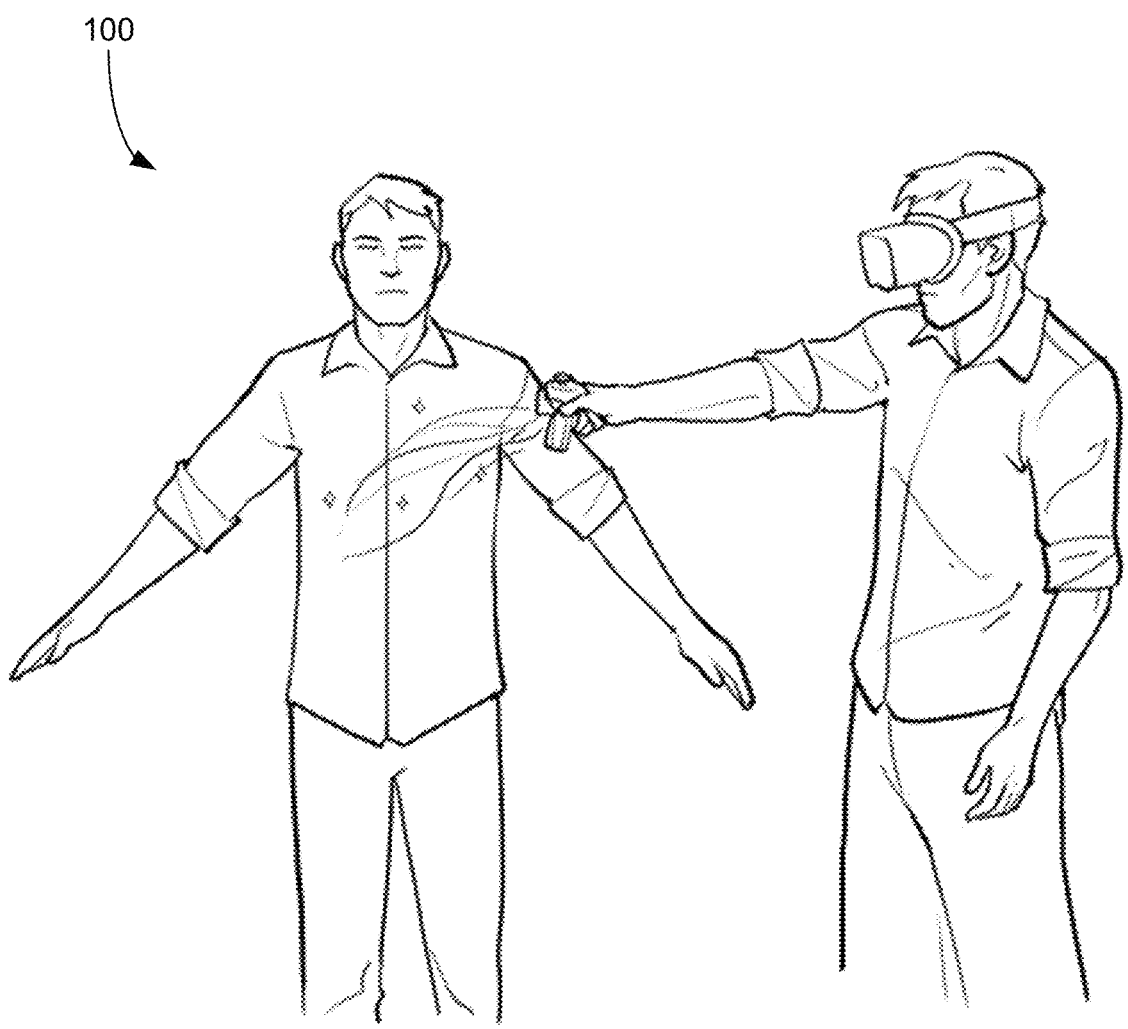
FIG. 1 illustrates an example of a user using a tool to treat a symptom area on the user's avatar in accordance with certain implementations of the disclosed technology.

FIG. 1 illustrates an example 100 of a user using a tool to treat a symptom area on the user's avatar in accordance with certain implementations of the disclosed technology. In the example, the user is using a handheld controller but one having ordinary skill in the art will appreciate that any suitable device may be used.

Figure 2:
FIG. 2 illustrates an example of a user representing a symptom area on the user's avatar in accordance with certain implementations of the disclosed technology.

FIG. 2 illustrates an example 200 of a user representing a symptom area on the user's avatar in accordance with certain implementations of the disclosed technology. In the example, the user is again using a handheld controller but one having ordinary skill in the art will appreciate that any suitable device may be used.

Figure 3:
FIG. 3 illustrates an example of a user and a clinician reviewing a user's symptom's progress over time on the user's avatar in accordance with certain implementations of the disclosed technology.

FIG. 3 illustrates an example 300 of a user and a clinician reviewing a user's symptom's progress over time on the user's avatar in accordance with certain implementations of the disclosed technology.

Figure 4:
FIG. 4 illustrates an example of a user mapping their pain sensation prior to wound care in accordance with certain implementations of the disclosed technology.

FIG. 4 illustrates an example 400 of a user mapping their pain sensation prior to wound care in accordance with certain implementations of the disclosed technology. In the example, the user is using a handheld controller to perform the mapping but it will be appreciated that one having ordinary skill in the art will readily recognize that any suitable device may be used.

Figure 5:
FIG. 5 illustrates an example of a clinician assisting a user by applying a treatment visualization or "erasing" a portion of the user's avatar in accordance with certain implementations of the disclosed technology.

FIG. 5 illustrates an example 500 of a clinician (i.e., the person wearing the darker shirt) assisting a user (i.e., the person who is seated) by applying a treatment visualization or "erasing" a portion of the user's avatar in accordance with certain implementations of the disclosed technology.

Example Case 1—Burn Therapy

In the example, a patient can use a virtual brush to sooth certain pain they are experiencing by way of any of a variety of suitable tools. The treatment may involve representing the targeted pain area and applying a visualization to the area intended to "counter" the represented pain, and may further include placing the patient into a distraction environment during wound care. Each tool can represent a different instrument of pain relief such as ointment, ice, bandages, and a healing wand, for example. Used in conjunction, the affected area may begin to visibly heal. The association of action to healing provides stimulus for psychological reduction of pain.

In the example, the user can embed their self in their avatar. Given the nature of burn therapy, this will likely be a seated or reclined representation. Embedding procedures may be tailored to each patient's ability at the time, and may be skipped or completed by a clinician if patient is incapacitated. This may include the clinician manipulating uninjured areas on behalf of the patient in a VR mirror environment, or alternatively mirrored tactile/haptic feedback. This will likely include passive embedding techniques such as respiration rate or heart rate feedback, for example.

In the example, the user may map/represent the targeted pain area visually. The user or clinician, if necessary, may draw pain using pain representation tools. Prior to and/or during wound care, pain treatment visualizations may be applied to the targeted pain area. This may continue procedurally (e.g., visualizations delivered automatically by the system) throughout the therapy. Pain therapy may include "erasure" of the target area—that is, the patient or clinician may "erase" visualization of the target pain area to distance perception of the targeted pain area by the mind during wound care. The patient may then experience distraction environments, e.g., certain experiences or games intended to distance the conscious mind and embedded experience from physical body sensation.

Example Case 2—Phantom Limb Pain

Phantom limb pain presents uniquely-reported cases that include nerve/electric pain, cramping or extended muscle contraction, and telescoping, e.g., the perception of the missing limb being compacted into the remaining limb at the point of amputation. Targeted therapies for phantom pain may include—but are not limited to—visualizations designed to treat the specific nature of the patient's pain.

In situations involving a telescoping limb, the patient may be presented with a virtual limb that is collapsed down to the point of amputation. Using a handheld controller, for example, the collapsed limb may be slowly pulled out of the virtual limb by the user. This action may provide a virtual view of the limb being back in its targeted location and may further advantageously provide relief from the perception of a collapsed limb.

Figure 6:
FIG. 6 illustrates an example of a user grasping a compressed telescoped limb at the base of the stump of the limb in accordance with certain implementations of the disclosed technology.

FIG. 6 illustrates an example 600 of a user grasping a compressed telescoped limb at the base of the stump of the limb in accordance with certain implementations of the disclosed technology.

Figure 7:
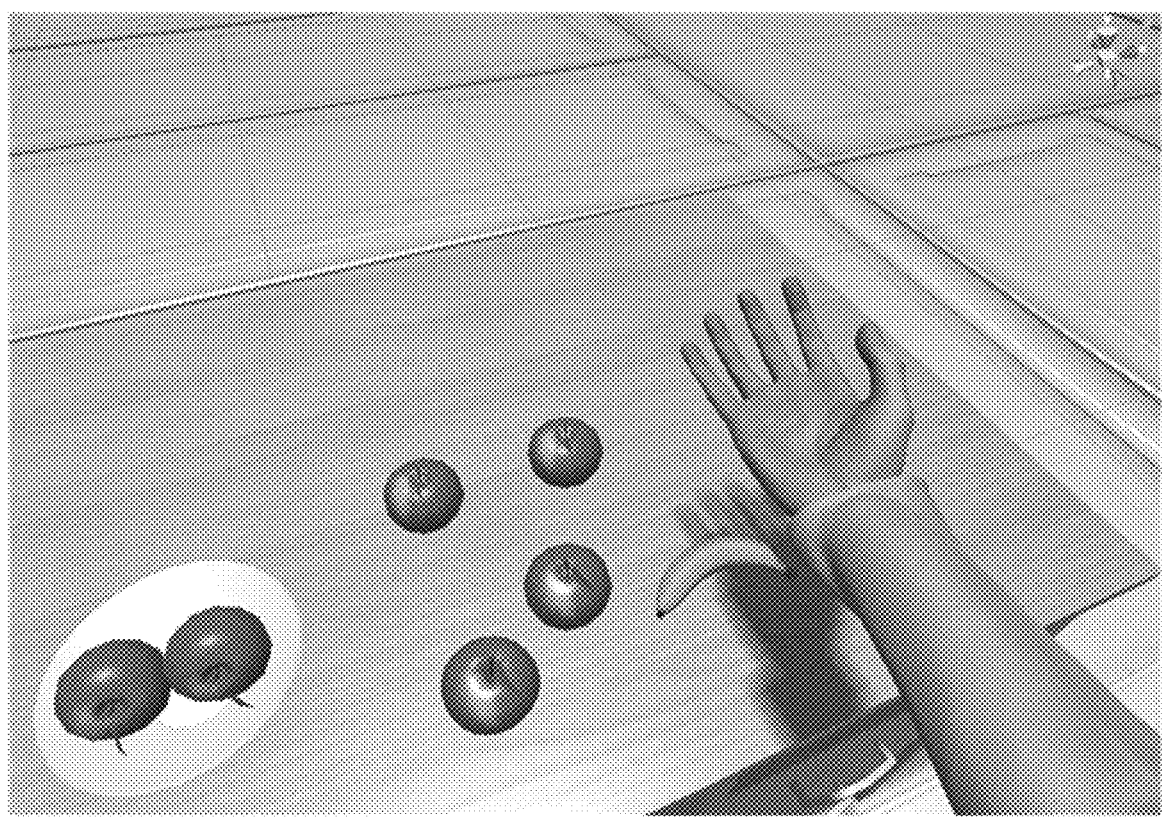
FIG. 7 illustrates an example of a virtual view of the user grasping the compressed telescoped limb at the base of the stump of the limb in accordance with certain implementations of the disclosed technology.

FIG. 7 illustrates an example 700 of a virtual view of the user grasping the compressed telescoped limb at the base of the stump of the limb in accordance with certain implementations of the disclosed technology.

Figure 8:
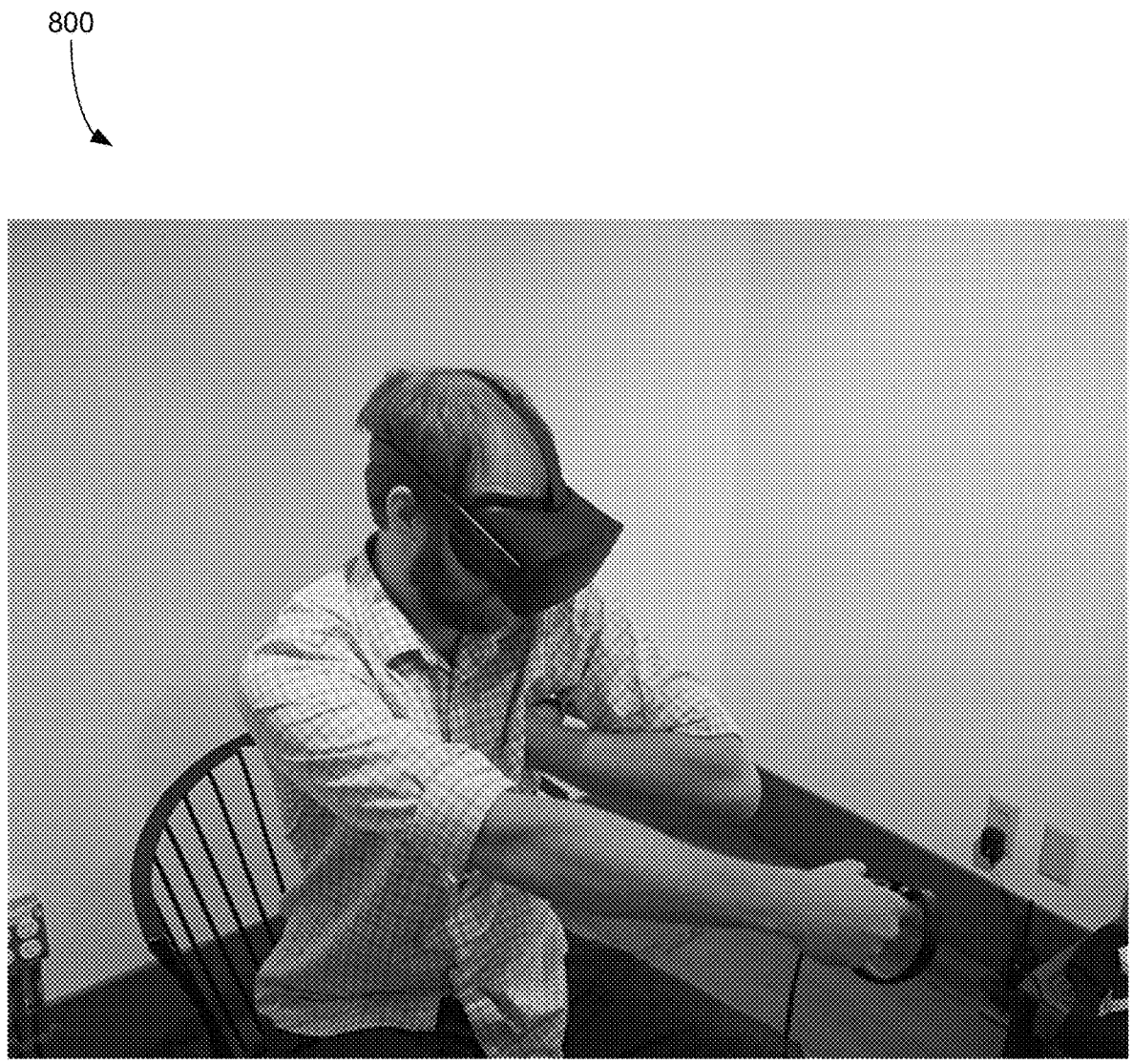
FIG. 8 illustrates an example of the user then pulling the limb out from the compressed position to its normal length in accordance with certain implementations of the disclosed technology.

FIG. 8 illustrates an example 800 of the user then pulling the limb out from the compressed position to its normal length in accordance with certain implementations of the disclosed technology.

Figure 9:
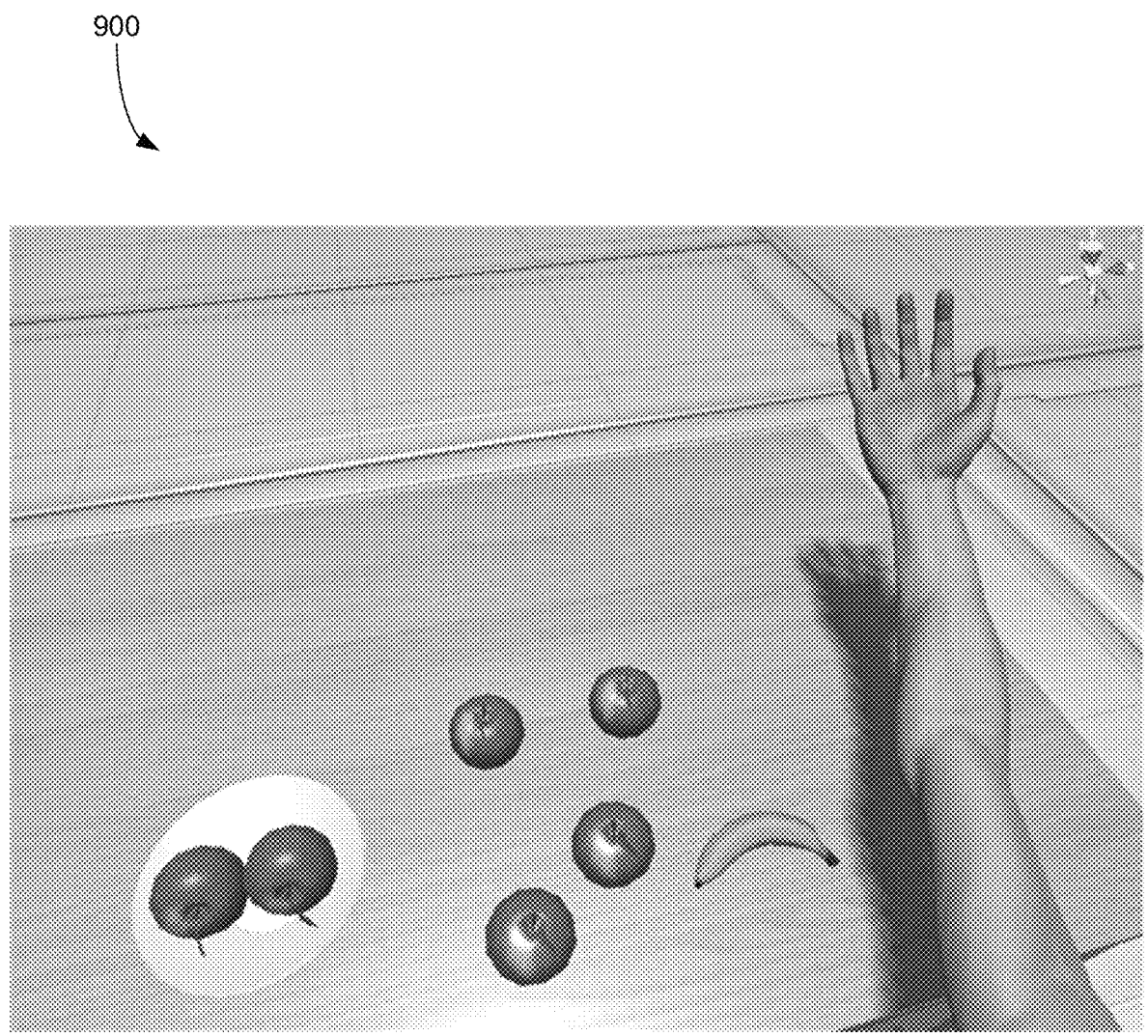
FIG. 9 illustrates an example of a virtual view of the user then pulling the limb out from the compressed position to its normal length in accordance with certain implementations of the disclosed technology.

FIG. 9 illustrates an example 900 of a virtual view of the user then pulling the limb out from the compressed position to its normal length in accordance with certain implementations of the disclosed technology.

In situations involving a phantom cramp or extended contraction, patients generally report extended contraction or cramping in their phantom limb. Using myoelectric control, the patient can see a representation of their limb, and may then "open" the hand.

Figure 10:
FIG. 10 illustrates an example of a user using a myoelectric armband to control a virtual limb in accordance with certain implementations of the disclosed technology.

FIG. 10 illustrates an example 1000 of a user using a myoelectric armband to control a virtual limb in accordance with certain implementations of the disclosed technology. In the example, the user's actual limb represents extended cramping.

Figure 11:
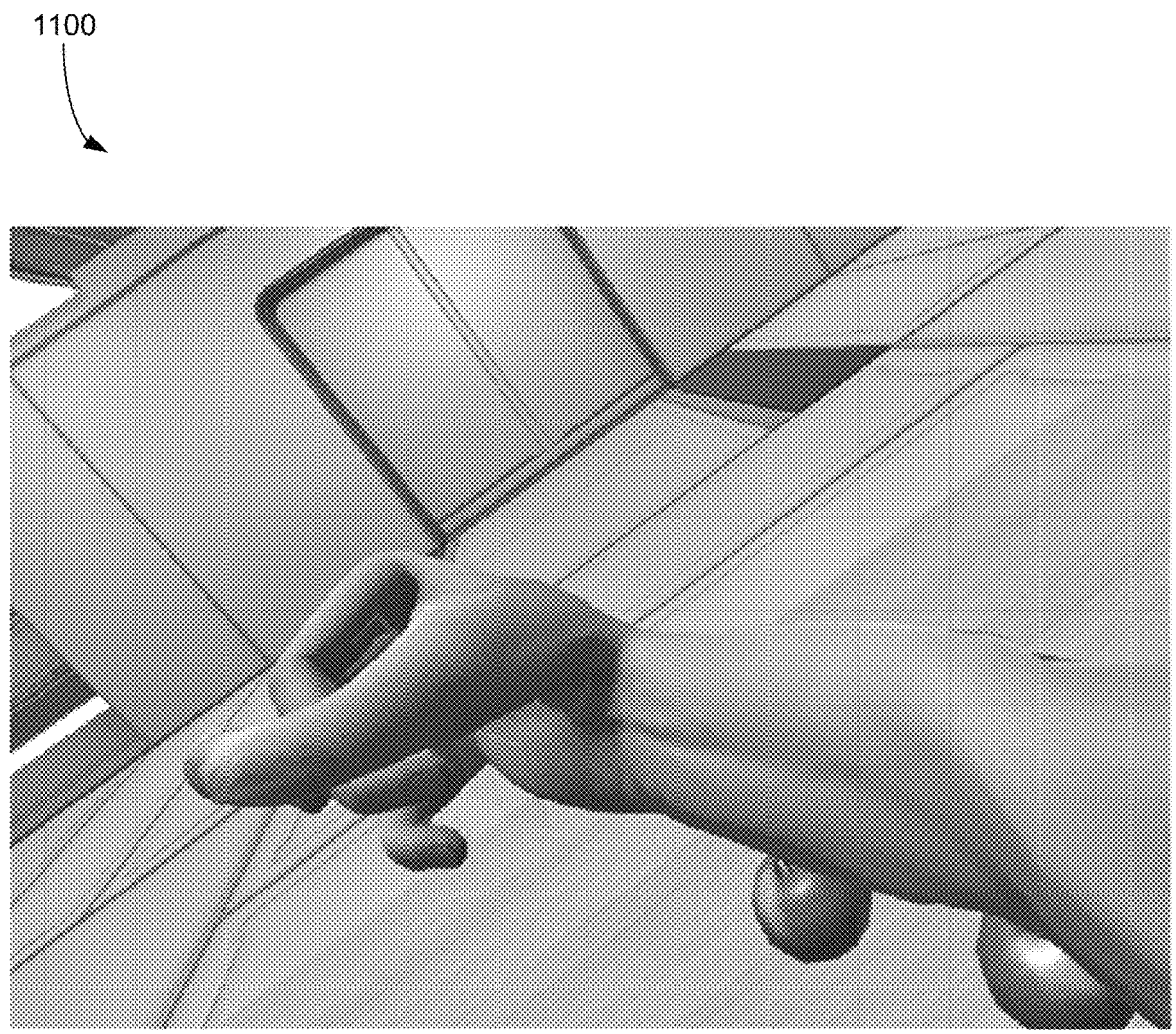
FIG. 11 illustrates an example of a virtual view of the user using the myoelectric armband to control the virtual limb in accordance with certain implementations of the disclosed technology.

FIG. 11 illustrates an example 1100 of a virtual view of the user using the myoelectric armband to control the virtual limb in accordance with certain implementations of the disclosed technology.

Figure 12:
FIG. 12 illustrates an example of the user using myoelectric controls to "opens" the virtual hand in accordance with certain implementations of the disclosed technology.

FIG. 12 illustrates an example 1200 of the user using myoelectric controls to "opens" the virtual hand in accordance with certain implementations of the disclosed technology. Such action may advantageously relieve the cramp.

Figure 13:
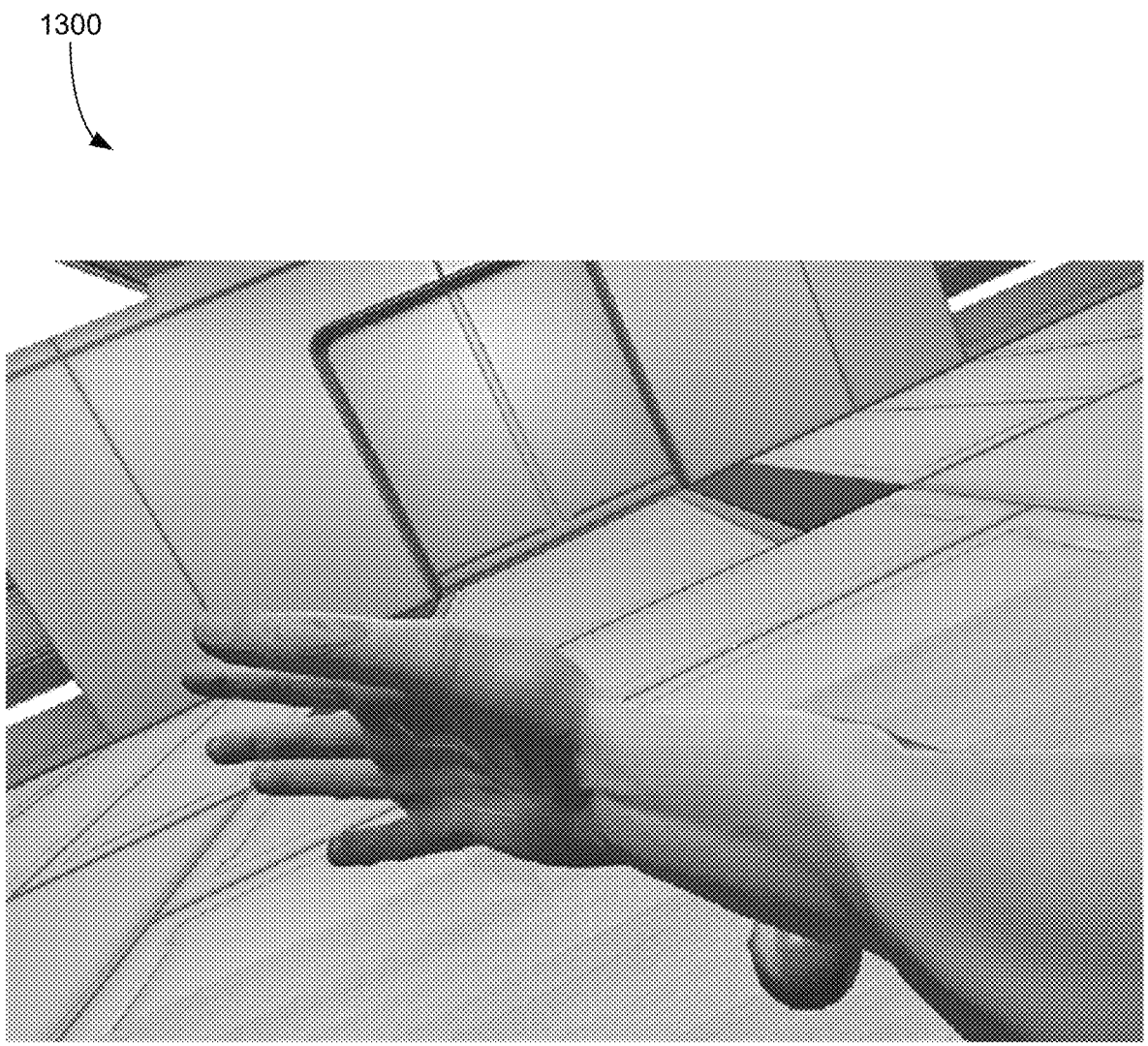
FIG. 13 illustrates an example of a virtual view of the user using the myoelectric controls to "opens" the virtual hand in accordance with certain implementations of the disclosed technology.

FIG. 13 illustrates an example 1300 of a virtual view of the user using the myoelectric controls to "opens" the virtual hand, thus relieving the cramp, in accordance with certain implementations of the disclosed technology.

Certain implementations may be directed to a neural network dynamic feature mapping of electromyography for the control of prosthetics. Control mapping and feature analysis of electromyography (EMG) where the EMG data is used in the control of prosthesis generally increases a user's ability to interact with the world through preprogrammed actions the arm can take; however, hard coded feature extraction is limited in overall accuracy. In the case of an upper arm amputation, for example, actions such as grabbing, elbow flexion/extension, wrist rotation, and others are generally provided by the prosthesis, giving the user concrete physical interaction with their surroundings.

Prior implementations of EMG analysis to drive such actions often misclassify the user's intent and perform actions counter to the user's intent, thus leading to lower adoption rates of prosthesis capable of providing the extended rage of actions. This issue is exacerbated as the number of possible output actions increase as each action drastically reduces the probability of accurate classifications.

These issues are advantageously solved by way of a novel neural network design implementing a connection between a series of Long Short Term Memory (LSTM) Neural Network and an Artificial Neural Network. Given incoming EMG data form an array of EMG devices, the network may output an action from an action tree. The desired action tree may be trained both by a large predefined database of EMG data and by way of direct training from the end user, which may provide a personalized action set with greater reliability of the intended action being classified accurately.

In certain implementations, an EMG data gathering device can be used to collect data, e.g., given it can produce samples at 50 Hz or greater. Transforming the data typically requires a simple configuration to specify the input data's upper range value. Additional scaling may be accomplished by way of a multiplicative operation along a curve proportional to the sensitivity of the EMG collection mechanism, for example. With this complete, the data may be normalized and ready to be passed into the system for classification.

The normalized output can be inputted into a first neural network model, e.g., used to classify individual muscle intent. In certain implementations, this LSTM network may take batches of a certain number of samples, e.g., 10 samples, from $x_i$ input sources and then use the data to classify active muscles and/or the intensity of each individual muscle. This step may provide the LSTM with an output that can correlate to intent via the mapped cluster of muscular activity over time. Using samples over time, the network may advantageously learn intended actions based on consecutive actions, rather than just the current EMG reading. The output generally has far less classification jitter as a result and may further provide smoother operation of the prosthesis.

The final step of classification may be a standard neural network which can take the output of LSTM and provide a layer of intent to predefined action mapping. During the training process, the LSTM may be fed intent based on perceived muscular activation, whereas the neural network may be fed the direct action mapping for animations the prosthesis can perform. The network may output both a classification and a rate value, e.g., used to drive the prosthesis animation and the speed at which the animation is run.

Configuration of the system inputs and outputs may be dynamic such that the count of incoming EMG channels and the number of output classifications can be updated, e.g., using the configuration file. This generally allows for larger system setups to have increasing accuracy such that each incoming channel of EMG data can be evaluated for an overall shift in output potential. Pretrained models for both muscle count and action verity typically reduce the training time for base model which learns muscle activation. The output array may also be configurable, e.g., such that it can be extended to allow for increasing output classification. The extra classification may then be used to drive the user action table.

Using this network design, correct classification for individual users may be greatly increased, as it generates unique feature sets for each user. The input EMG data may drive the formation of features over iterations of the derivative of the loss function (i.e., mean squared error) in relation to predefined action table items. As this data is unique to the user, the system may find the optimal action given enough iterations on the training data.

Certain implementations of the disclosed technology may include a method for applying and delivering sensory data to and from real-time three-dimensional (3D) objects. Objects that are rendered in real-time 3D environments such as the Unity or Unreal engine generally incorporate multiple layers of various types of information such as lighting effects, textures, materials etc. These different types of data generally indicate how a 3D object interacts or can interact with its environment and/or a user. For example, lighting effects typically dictate how light will bounce off of an object, e.g., metallic, chrome, or matte, for example. Textures and materials may provide information as to how the object will or can interact with the physics that are built into or otherwise established within the real-time environment.

Certain implementations may include integration of a separate layer of data—e.g., a dataset applied to the 3D file itself—for sensory information. Neural sensory input/output (TO) is currently viable via "neural sensory IO devices" such as Neural Cuffs, for example. These devices are intended, primarily, for use in advanced prosthetic devices. Since these devices generally offer direct neural IO they can deliver and send specific electrical signals to the neural system of the user.

Certain implementations may include delivering signals to a user using these types of devices from a real-time environment, e.g., VR and/or AR headsets. A user may have a neural IO device and the user may be able to receive and/or send data from this device. Using the same signals that are delivered to the user by way of interactions in the real world space, the disclosed tools and techniques may include taking these signals (e.g., Sensory Data) and applying the sensory data to 3D real-time objects as an embedded file in the object.

The user may then enter a virtual environment, such as an Oculus environment, and the virtual environment may deliver sensory data to the user based on the user's actions. The virtual environment may further deliver data back to the real-time environment based on user actions, for example.

In certain examples where a user picks up a 3D object that looks like a cold glass of water, the coding of that 3D object may be configured to deliver data for "cold," "smooth," and "solid" attributes/characteristics, etc.

Certain implementations may include a separate filetype that may be added to the real-time 3D model.

Figure 14:
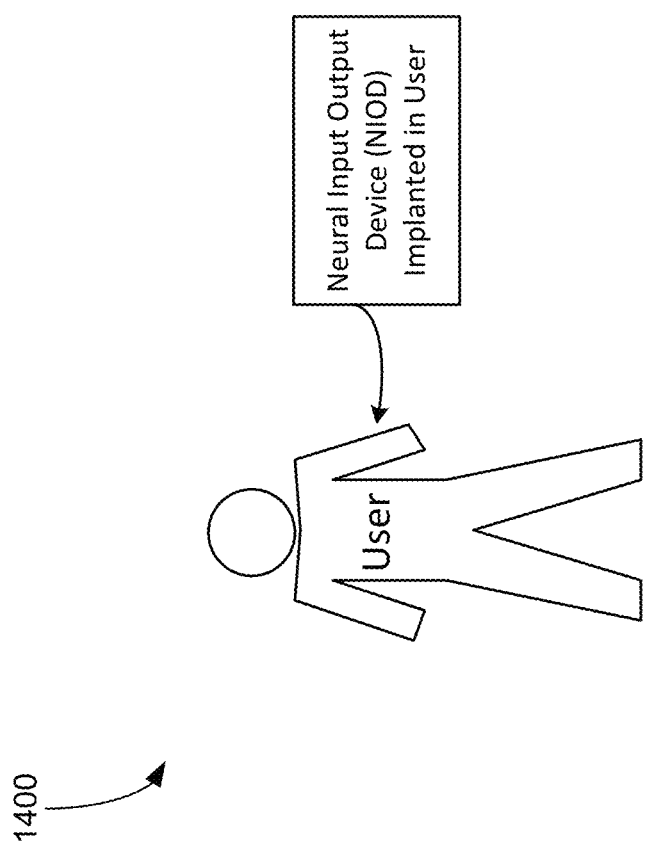
FIG. 14 illustrates an example of a neural input/output device (NIOD) in accordance with certain implementations of the disclosed technology.

FIG. 14 illustrates an example 1400 of a neural input/output device (NIOD) in accordance with certain implementations of the disclosed technology. In the example, the NIOD is implanted in the user.

Figure 15:
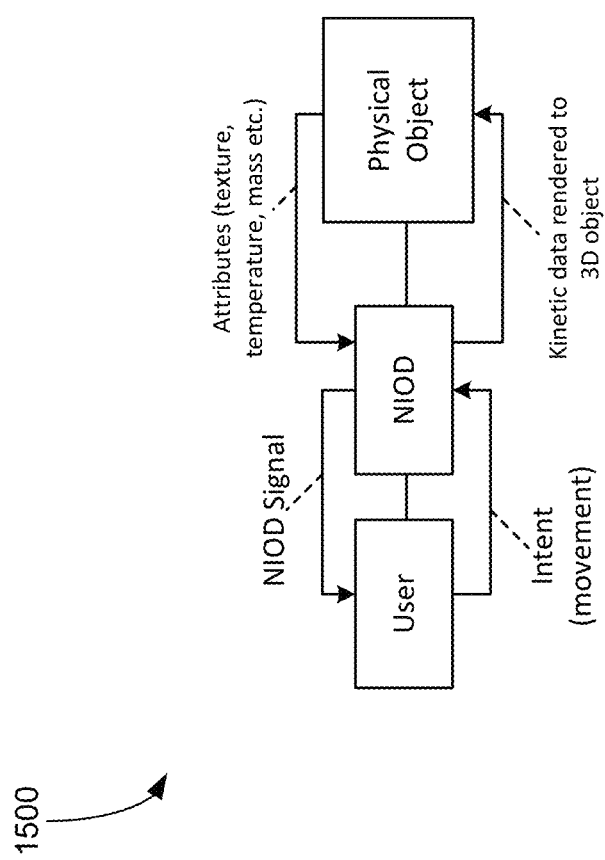
FIG. 15 illustrates an example of a NIOD such as the NIOD illustrated by FIG. 14 interacting with a physical object in accordance with certain implementations of the disclosed technology.

FIG. 15 illustrates an example 1500 of a NIOD such as the NIOD illustrated by FIG. 14 interacting with a physical object in accordance with certain implementations of the disclosed technology. In the example, a NIOD signal is provided to the user and an intent (e.g., movement) is provided to the NIOD. Attributes of the physical object (such as texture, temperature, and mass, for example) are provided to the NIOD and kinetic data is rendered to the 3D object.

Figure 16:
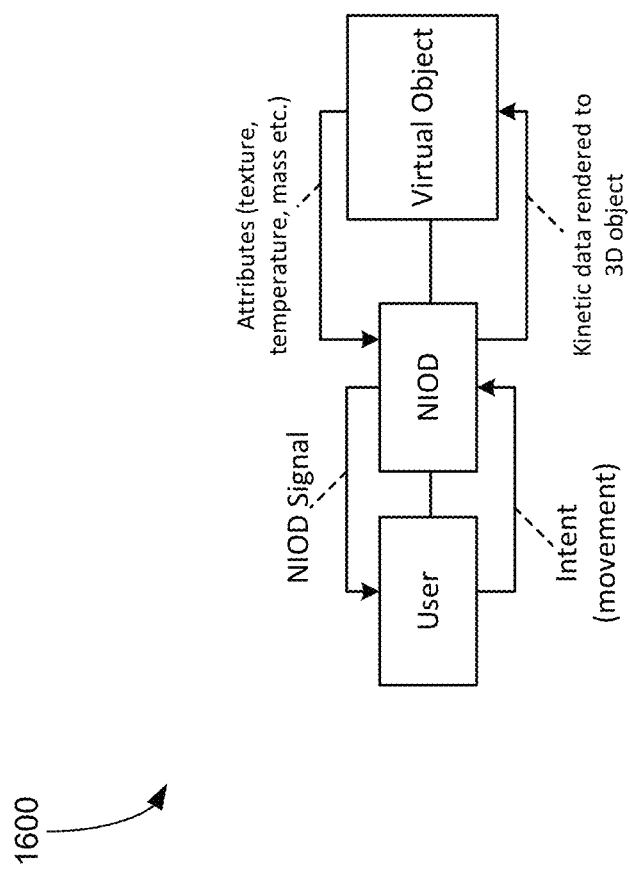
FIG. 16 illustrates an example of a NIOD such as the NIOD illustrated by FIG. 14 interacting with a virtual object in accordance with certain implementations of the disclosed technology.

FIG. 16 illustrates an example 1600 of a NIOD such as the NIOD illustrated by FIG. 14 interacting with a virtual object in accordance with certain implementations of the disclosed technology. In the example, a NIOD signal is provided to the user and an intent (e.g., movement) is provided to the NIOD. Attributes of the virtual object (such as texture, temperature, and mass, for example) are provided to the NIOD and kinetic data is rendered to the 3D object.

Figure 17:
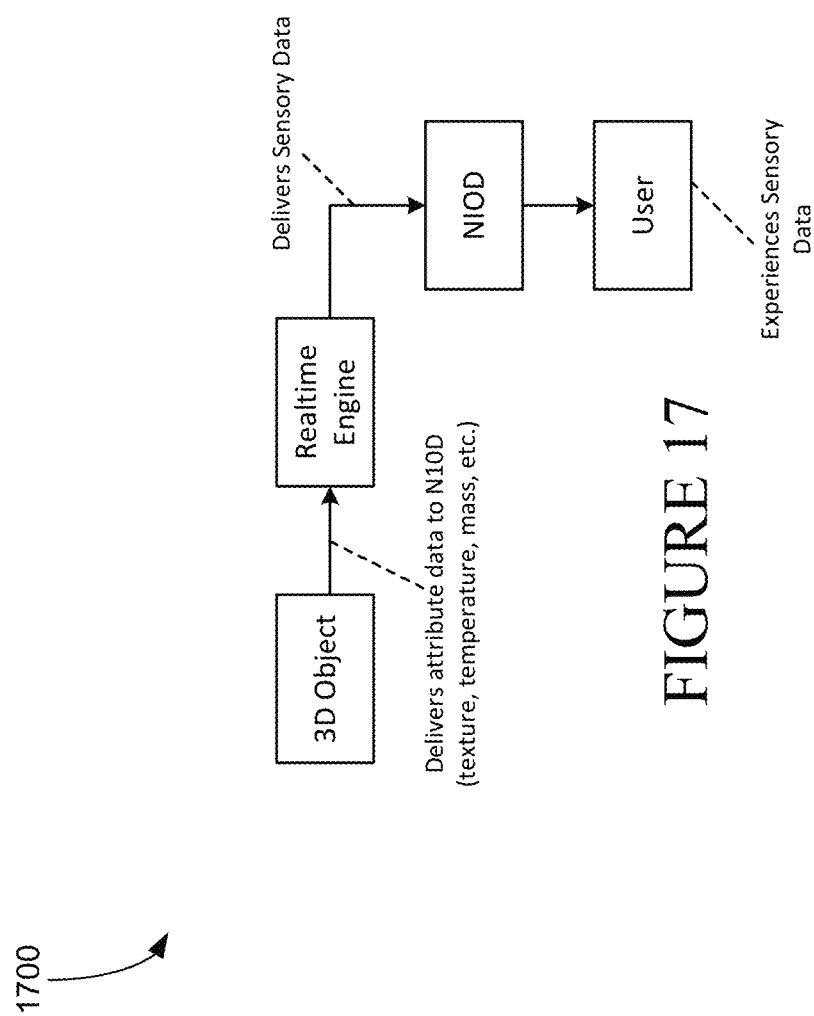
FIG. 17 illustrates an example of a NIOD such as the NIOD illustrated by FIG. 14 interacting with a real-time engine in accordance with certain implementations of the disclosed technology.

FIG. 17 illustrates an example 1700 of a NIOD such as the NIOD illustrated by FIG. 14 interacting with a real-time engine in accordance with certain implementations of the disclosed technology.

Figure 18:
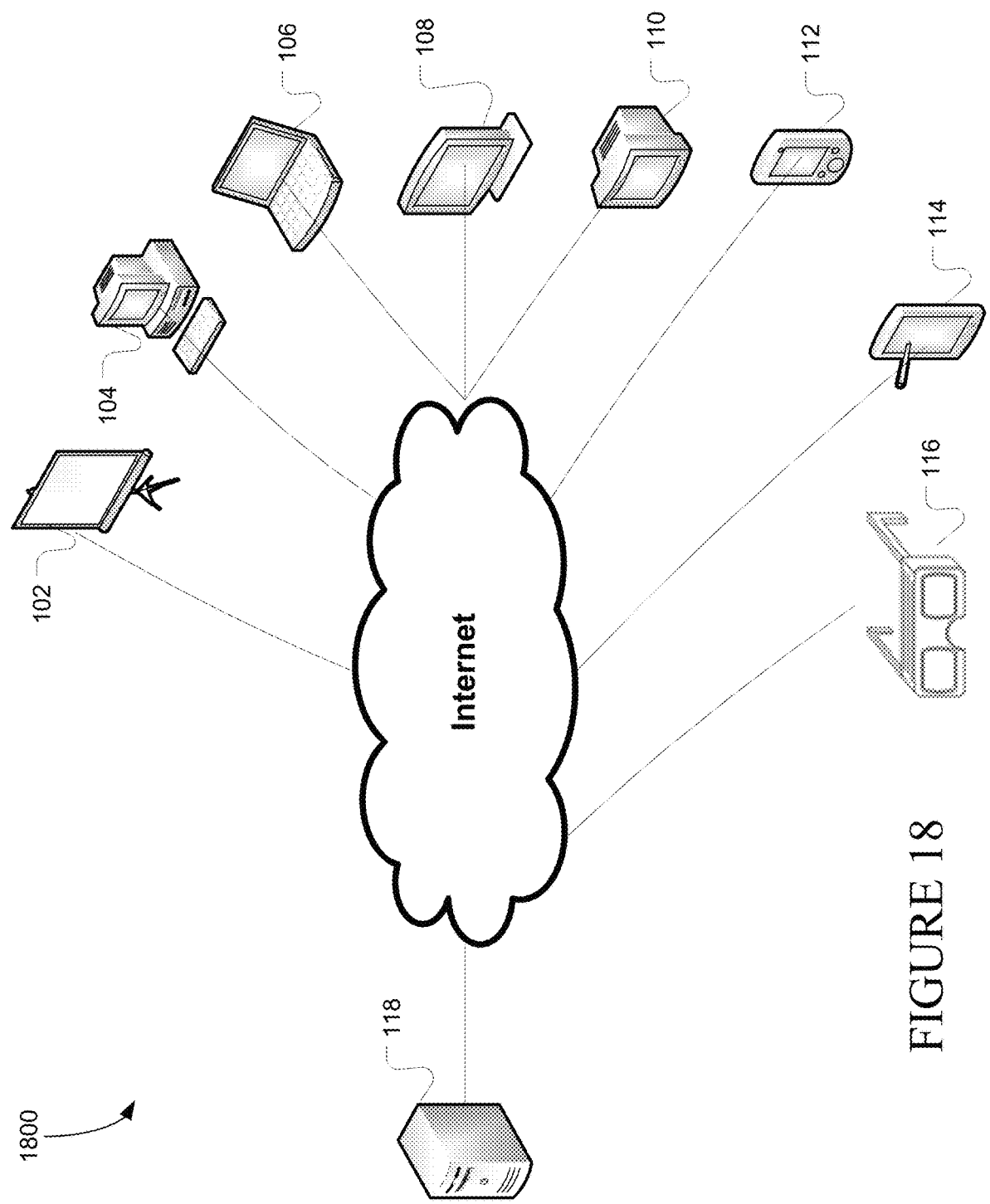
FIG. 18 illustrates an example of a system 1800 suitable for supporting any or all of the embodiments disclosed herein in accordance with certain implementations of the disclosed technology.

FIG. 18 illustrates an example of a system 1800 suitable for supporting any or all of the embodiments disclosed herein in accordance with certain implementations of the disclosed technology. In the example, a number of different devices are available for a user to use, such as a desktop computer 104, a laptop computer 106, a mobile and/or smart phone 112, a television 110, a tablet device 114, virtual reality goggles 116, a projector screen 102, and other computing devices 108. It should be understood that these devices may be used in isolation or in any combination with other devices.

The disclosed aspects may be implemented, in some cases, in hardware, firmware, software, or any combination thereof. The disclosed aspects may also be implemented as instructions carried by or stored on one or more or non-transitory computer-readable media, which may be read and executed by one or more processors. Such instructions may be referred to as a computer program product. Computer-readable media, as discussed herein, means any media that can be accessed by a computing device. By way of example, and not limitation, computer-readable media may comprise computer storage media and communication media.

Additionally, this written description makes reference to particular features. It is to be understood that the disclosure in this specification includes all possible combinations of those particular features. For example, where a particular feature is disclosed in the context of a particular aspect, that feature can also be used, to the extent possible, in the context of other aspects.

Also, when reference is made in this application to a method having two or more defined steps or operations, the defined steps or operations can be carried out in any order or simultaneously, unless the context excludes those possibilities.

Furthermore, the term "comprises" and its grammatical equivalents are used in this disclosure to mean that other components, features, steps, processes, operations, etc. are optionally present. For example, an article "comprising" or "which comprises" components A, B, and C can contain only components A, B, and C, or it can contain components A, B, and C along with one or more other components.

Also, directions such as "right" and "left" are used for convenience and in reference to the diagrams provided in figures. But the disclosed subject matter may have a number of orientations in actual use or in different implementations. Thus, a feature that is vertical, horizontal, to the right, or to the left in the figures may not have that same orientation or direction in all implementations.

Having described and illustrated the principles of the invention with reference to illustrated embodiments, it will be recognized that the illustrated embodiments may be modified in arrangement and detail without departing from such principles, and may be combined in any desired manner. And although the foregoing discussion has focused on particular embodiments, other configurations are contemplated.

In particular, even though expressions such as "according to an embodiment of the invention" or the like are used herein, these phrases are meant to generally reference embodiment possibilities, and are not intended to limit the invention to particular embodiment configurations. As used herein, these terms may reference the same or different embodiments that are combinable into other embodiments.

Although specific embodiments of the invention have been illustrated and described for purposes of illustration, it will be understood that various modifications may be made without departing from the spirit and scope of the invention. Accordingly, the invention should not be limited except as by the appended claims.

What is claimed is:

1. A method, comprising:
   mapping an avatar of a user to a physical body of the user;
   rendering, in a virtual environment displayed on a virtual reality headset, a compressed telescoped limb at a base of a stump of the compressed telescoped limb;
   detecting the user grasping the rendered compressed telescoped limb at a base of a stump of the compressed telescoped limb; and
   providing a virtual view of the user pulling the rendered compressed telescoped limb out to its normal length via the virtual reality headset.

* * * * *